United States Patent
Mercadal et al.

(10) Patent No.: US 6,422,813 B1
(45) Date of Patent: Jul. 23, 2002

(54) APPARATUS FOR PRODUCING VIBRATION IN TURBO-MACHINERY BLADES

(75) Inventors: Mathieu Mercadal; Cory Roeseler; Andreas von Flotow, all of Hood River, OR (US)

(73) Assignee: Hood Technology Corporation, Hood River, OR (US)

( * ) Notice: Subject to any disclaimer, the term of this patent is extended or adjusted under 35 U.S.C. 154(b) by 52 days.

(21) Appl. No.: 09/651,677

(22) Filed: Aug. 30, 2000

Related U.S. Application Data

(60) Provisional application No. 60/152,411, filed on Sep. 3, 1999.

(51) Int. Cl.[7] ............................................. F01D 25/04
(52) U.S. Cl. ........................... 415/119; 415/1; 416/500
(58) Field of Search ............................. 415/1, 119, 914, 415/9; 416/900

(56) References Cited

U.S. PATENT DOCUMENTS

| | | | | |
|---|---|---|---|---|
| 5,365,663 A | * | 11/1994 | Demartini | 29/889.21 |
| 5,709,527 A | * | 1/1998 | Ernst et al. | 415/10 |
| 6,050,782 A | * | 4/2000 | Lembke | 417/205 |
| 6,094,989 A | * | 8/2000 | Twerdochlib | 73/659 |

* cited by examiner

Primary Examiner—Edward K. Look
Assistant Examiner—James M McAleenan
(74) Attorney, Agent, or Firm—Bell, Boyd & Lloyd LLC

(57) ABSTRACT

A realistic study of high-cycle fatigue in turbo-machinery is dependent on a means of reproducing, in an evacuated test facility, the vibration of turbine blades caused by inhomogeneous flow in the engine. An apparatus and method are described which use magnetic eddy currents to generate such vibration. The apparatus makes use of an array of magnets to produce blade vibration of the magnitude and period characteristic for turbo-machines.

10 Claims, 7 Drawing Sheets

APPARATUS FOR PRODUCING VIBRATION IN TURBO-MACHINERY BLADES

The present application is directly related to U.S. Provisional Patent Application No. 60/152,411, filed Sep. 3, 1999, the entire contents of which are hereby incorporated by reference and relied upon.

BACKGROUND OF THE INVENTION

1. Field of the Invention

The present application discloses a method and an apparatus for causing excitation of turbo-machinery blades that reproduces the vibrational effects of stator wakes and other turbulent airflow. The method and apparatus comprise generating eddy currents in the blades by an array of magnets to produce appropriate forces.

2. Description of the Related Art

Avoidance of fatigue failure is a major factor in turbo-machinery maintenance and replacement. High-cycle fatigue results from resonant modes in the rotor blades and synchronous excitation of such resonant modes. The turbulent wakes trailing from stator vanes are a leading cause of blade vibration. FIG. 1 illustrates the relation between upstream stators and turbine blades in turbo-machinery. Stator vanes create turbulent wakes that cause vibration in turbine blades. In order to study such effects, blade vibration must be reproduced in an evacuated test facility. FIG. 2 illustrates the evacuated spin pit in which blade vibration is to be reproduced.

In order to stimulate the modes of vibration experienced in turbines, an appropriate means of excitation is required. Several methods have been used or proposed. They include air jets, electromagnets operating on ferro-magnetic blades or ferro-magnetic patches of material, piezo-ceramic patches, vibration of the entire hub-blade system, and fluid jets. FIG. 3 illustrates these alternatives, and also notes the deficiencies of each one.

SUMMARY OF THE INVENTION

The present application discloses a method and an apparatus for causing excitation of turbo-machinery blades that reproduces the vibrational effects of stator wakes and other inhomogeneous airflow. The method comprises positioning an array of magnets near turbo-machinery blades to generate eddy currents in the blades to produce appropriate forces.

In preferred embodiments of the method, the magnets are positioned so as to obtain periodic vibration of the blades equivalent to that from stator wakes; the array of magnets are configured to appropriately phase an excitation force applied to various portions of the blades such that a particular target mode of vibration is strongly excited; the magnets are repositioned relative to passing blades to control the excitation force; and the array of magnets is designed with reference to a computational model of an unsteady magnetic interaction.

The apparatus for causing excitation of turbo-machinery blades that reproduces the vibrational effects of stator wakes and other inhomogeneous airflow comprises means for generating eddy currents in the blades by an array of magnets to produce appropriate forces.

In preferred embodiments of the apparatus, the magnets are positioned so as to obtain periodic vibration of the blades equivalent to that from stator wakes; the array of magnets are configured to appropriately phase an excitation force applied to various portions of the blades such that a particular target mode of vibration is strongly excited; the magnets are repositioned relative to passing blades to control the excitation force; and the array of magnets is designed with reference to a computational model of an unsteady magnetic interaction.

Detailed Description of the Invention

The apparatus described here uses the phenomenon of magnetic eddy currents to create controlled excitation in turbine blades passing appropriately positioned magnets. Although turbine blades are typically constructed from non-magnetic or weakly magnetic material, nonetheless magnetic eddy currents can exert significant forces. Under mild assumptions (see *Low Frequency Electromagnetic Design*, Michael P. Perry, 1985, Marcel Dekker, Inc.), the magnetic field variation in a moving conductor can be described by the following diffusion equation:

$$\nabla^2 \vec{B} = \mu\sigma\left(\frac{\partial}{\partial t} + \vec{v}\cdot\nabla\right)\vec{B} \qquad \text{Eq. 1}$$

The equation is often made non-dimensional using characteristic length and frequency:

$$[x,y,z]=[\hat{x},\hat{y},\hat{z}]L \qquad \text{Eq. 2}$$

where L is a characteristic length $$\nabla = \hat{\nabla}\frac{1}{L} \qquad \text{Eq. 3}$$

$$t = \hat{t}\frac{1}{\omega} \text{ where } \omega \text{ is a characteristic frequency} \qquad \text{Eq. 4}$$

$$v=\hat{v}L\omega \qquad \text{Eq. 5}$$

Substituting into Eq. 1, we get the following dimensionless equation $$\hat{\nabla}^2 \vec{B} = \mu\sigma L^2 \omega \left(\frac{\partial}{\partial \hat{t}} + \hat{\vec{v}} \cdot \hat{\nabla}\right) \vec{B} \qquad \text{Eq. 6}$$

which depends on a dimensionless parameter, the magnetic Reynolds number:

$$R_m = \frac{1}{2}\mu\sigma L^2 \omega \qquad \text{Eq. 7}$$

An important quantity appearing in the magnetic Reynolds number is the skin penetration depth to which the conductor is affected by an unsteady magnetic field:

$$l = \frac{\sqrt{2}}{\sqrt{\omega\mu\sigma}} \qquad \text{Eq. 8}$$

For reference, the penetration depth for a sinusoidal magnetic field varying at 2,000 Hz is:

$l = 7.5$ mm, Titanium, 2000 Hz $= 1.8$ mm, Aluminum, 2000 Hz

The equivalent "R/L pole" is also often used to describe whether a problem is low frequency, where magnetic fields may be considered quasi-static, or high frequency where magnetic field propagation is limited by the distributed inductance of a material:

$\omega_{critical} = 12.4$ kHz, Titanium, 3 mm $= 700$ Hz, Aluminum, 3 mm

Figure 1:
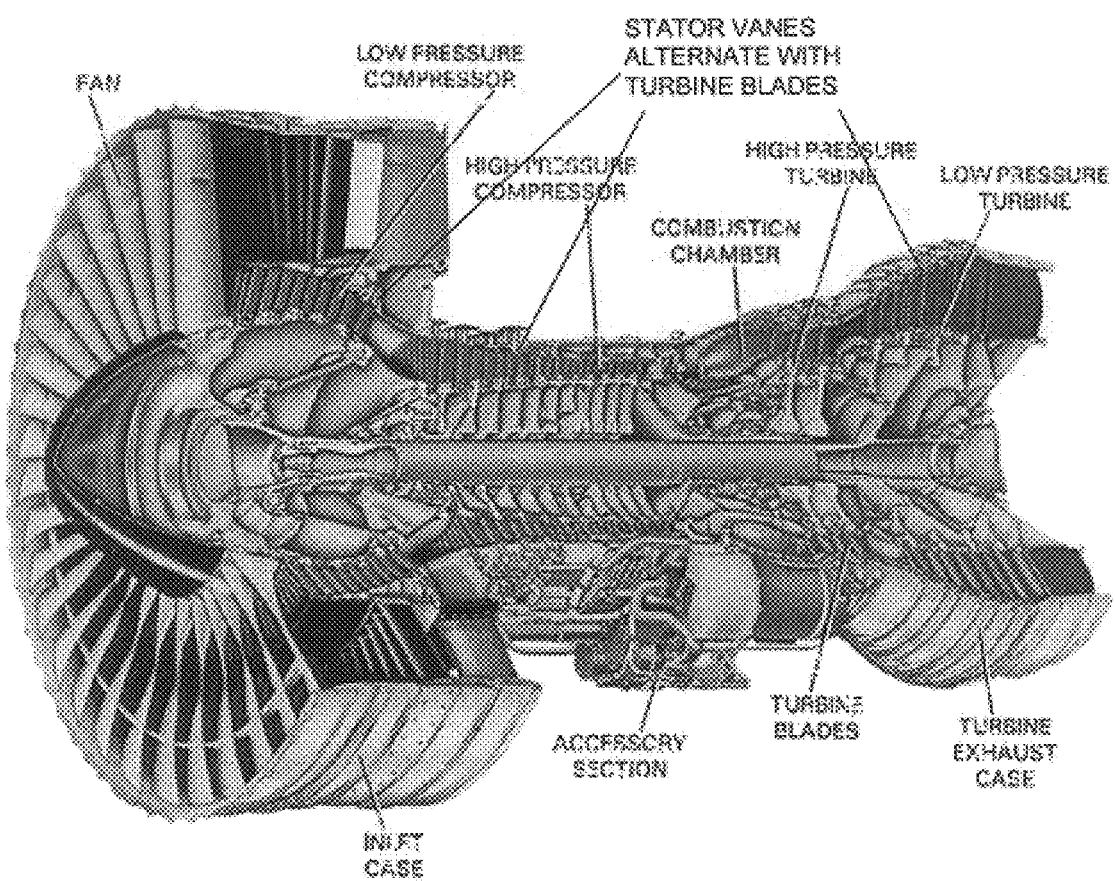
FIG. 1 shows stator vanes alternating with turbine blades in turbo-machinery.
Figure 2:
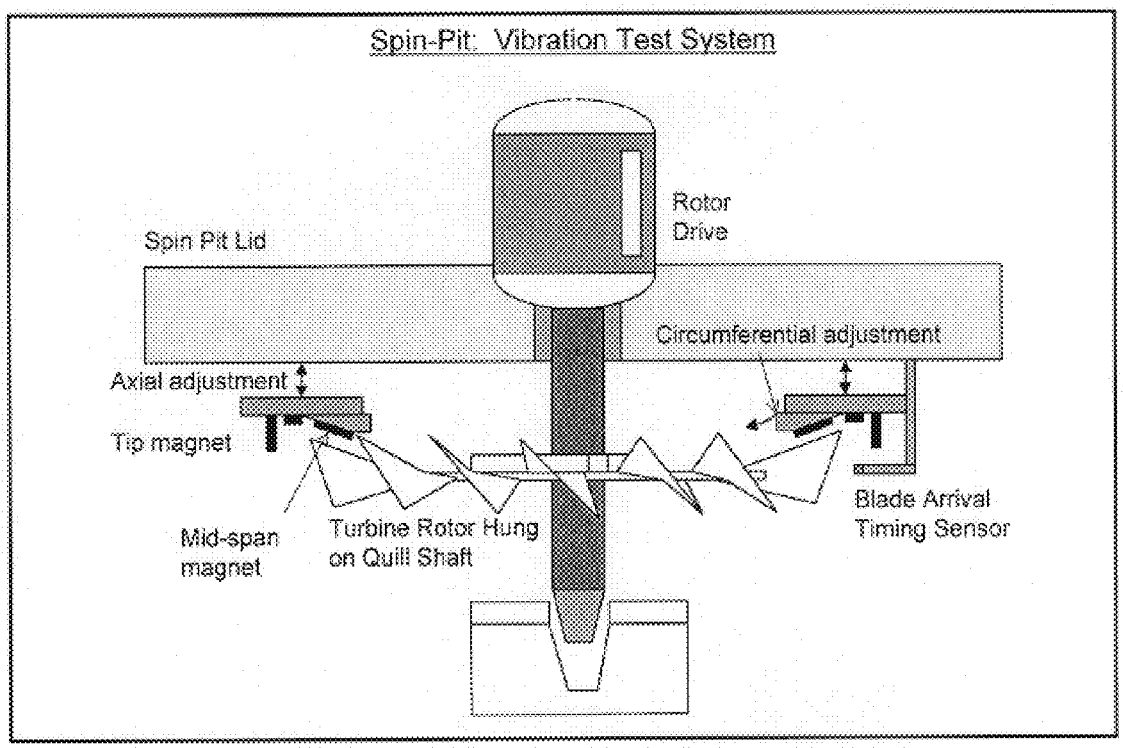
FIG. 2 illustrates an evacuated spin pit in which blade vibration is to be reproduced.
Figure 3:
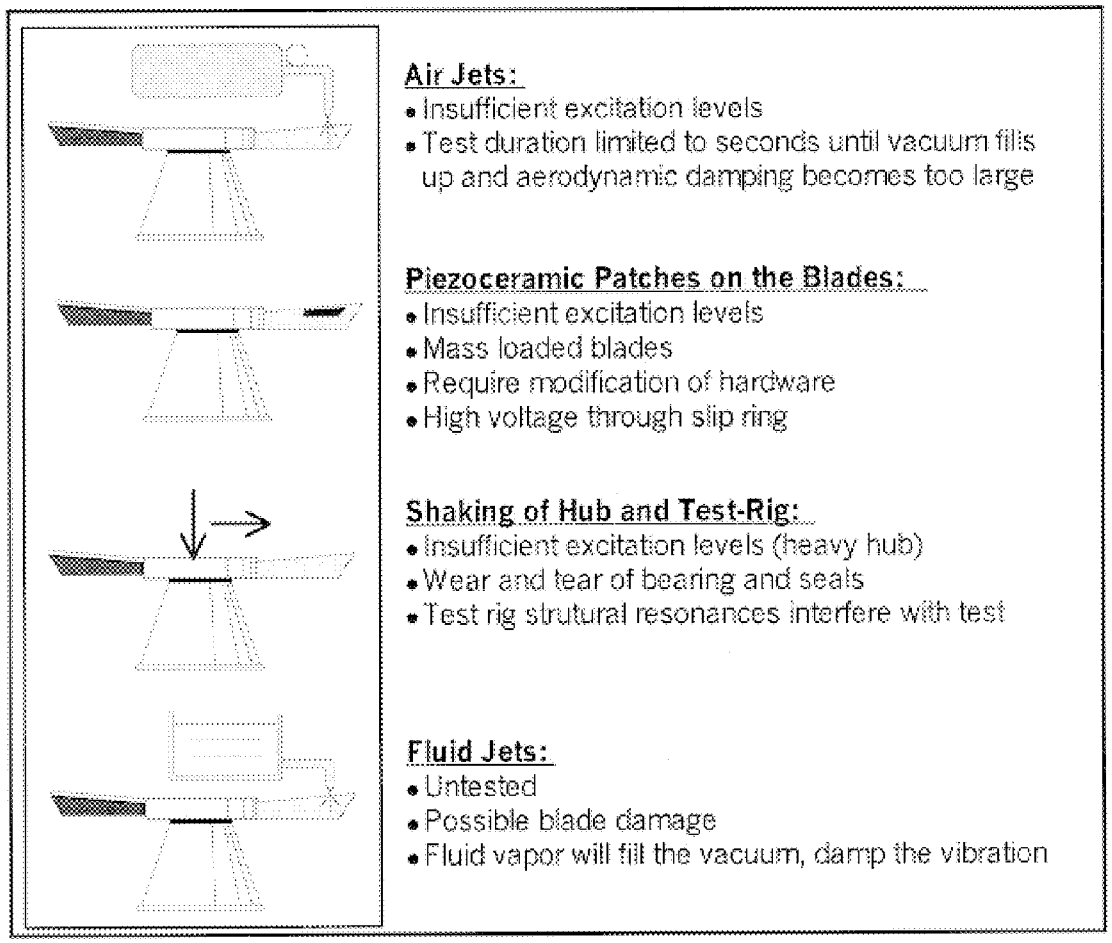
FIG. 3 illustrates alternative methods of exciting vibration in turbine blades.
Figure 4:
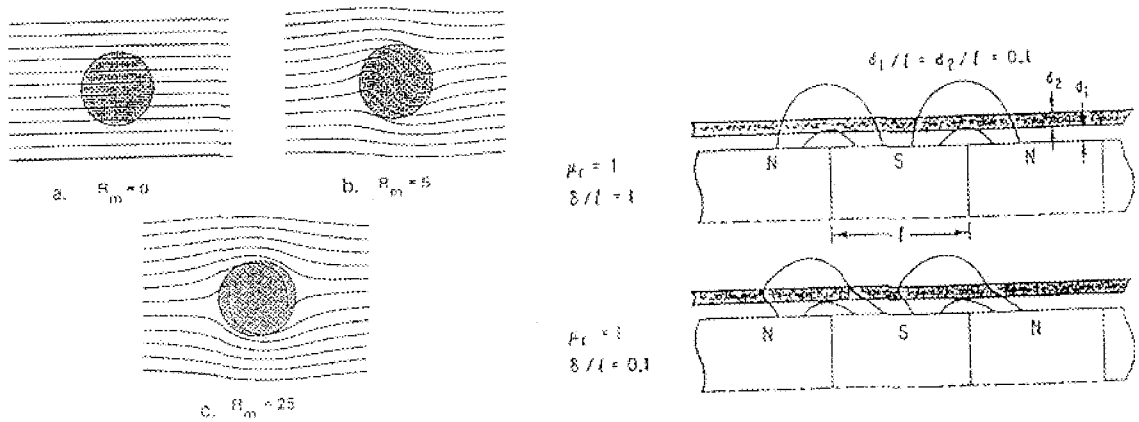
FIG. 4 shows flux lines in a spinning conductive bar (left) and in a moving conductive sheet (right). *Low Frequency Electromagnetic Design*, Michael P. Perry, 1985, Marcel Dekker, Inc.

In order to apply these results to estimate forces on a turbine blade, one can determine how much the magnetic field is "deflected" by the passing blade. From this deflected field, one can calculate the instantaneous force acting on the blade in a given direction. Visualization of the deflected field helps in understanding the phenomenon. FIG. 4 shows solutions for a rotating bar in a magnetic field and for a continuous conductive sheet moving over a magnetic field.

At slow speeds, skin penetration is large compared to the dimension of the moving conductor, and force acting to oppose blade motion is partly dissipated as heat in the blade. This requires increased torque to spin the turbine as its blades travel past the magnet.

At higher speeds, skin penetration is small compared to the dimension of the blade, and the force acts to repel the motion. As the blade approaches, force generated by the magnetic field opposes motion. When the blade is over the magnet, the force is repulsive and orthogonal to travel. As the blade travels away from the magnet, existing eddy currents in the blade cause forces that act in the direction of travel. A description of this sequence might be "drag-repel-push." Note that no net work is done as the "drag" and "push" force histories are equal and opposite and the "repel" force acts orthogonal to motion.

Figure 7:
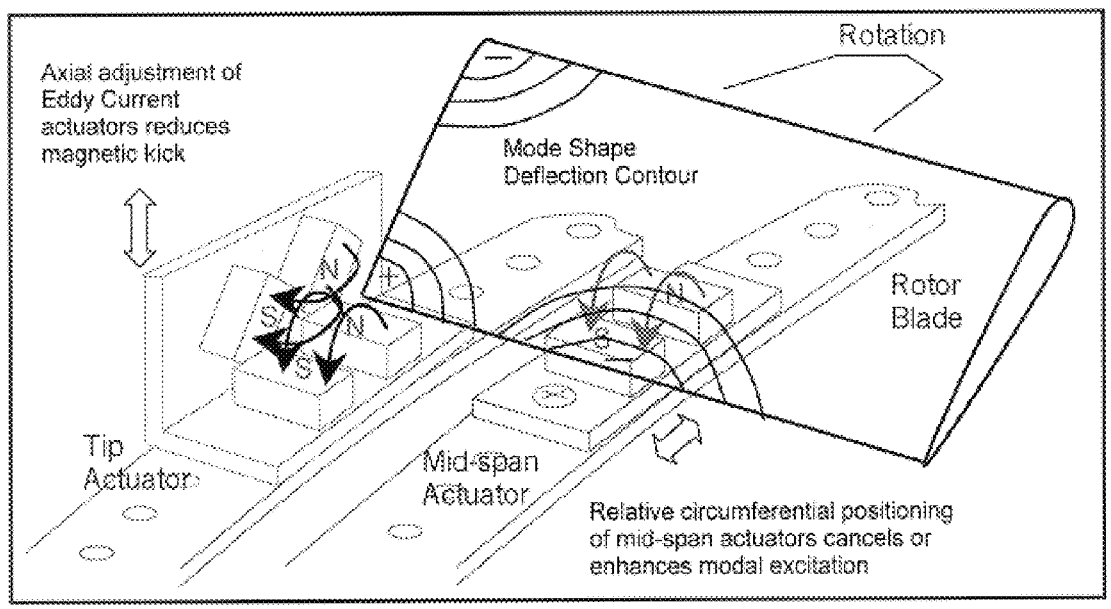
FIG. 7 illustrates the basic concept of the eddy current apparatus for exciting vibration in turbine blades.

FIG. 7 illustrates the basic concept of the eddy current apparatus for exciting vibration in turbine blades. Magnets along the blade edge are positioned using a clocking mechanism to create the appropriate phasing. Excitation occurs as eddy currents are generated in the fast-moving blades moving through the drag-repel-push cycle described above. Vibration of the period and magnitude typical of high-speed turbines can be obtained, providing the experimental conditions necessary to study high-cycle fatigue in turbomachinery.

Figure 5:
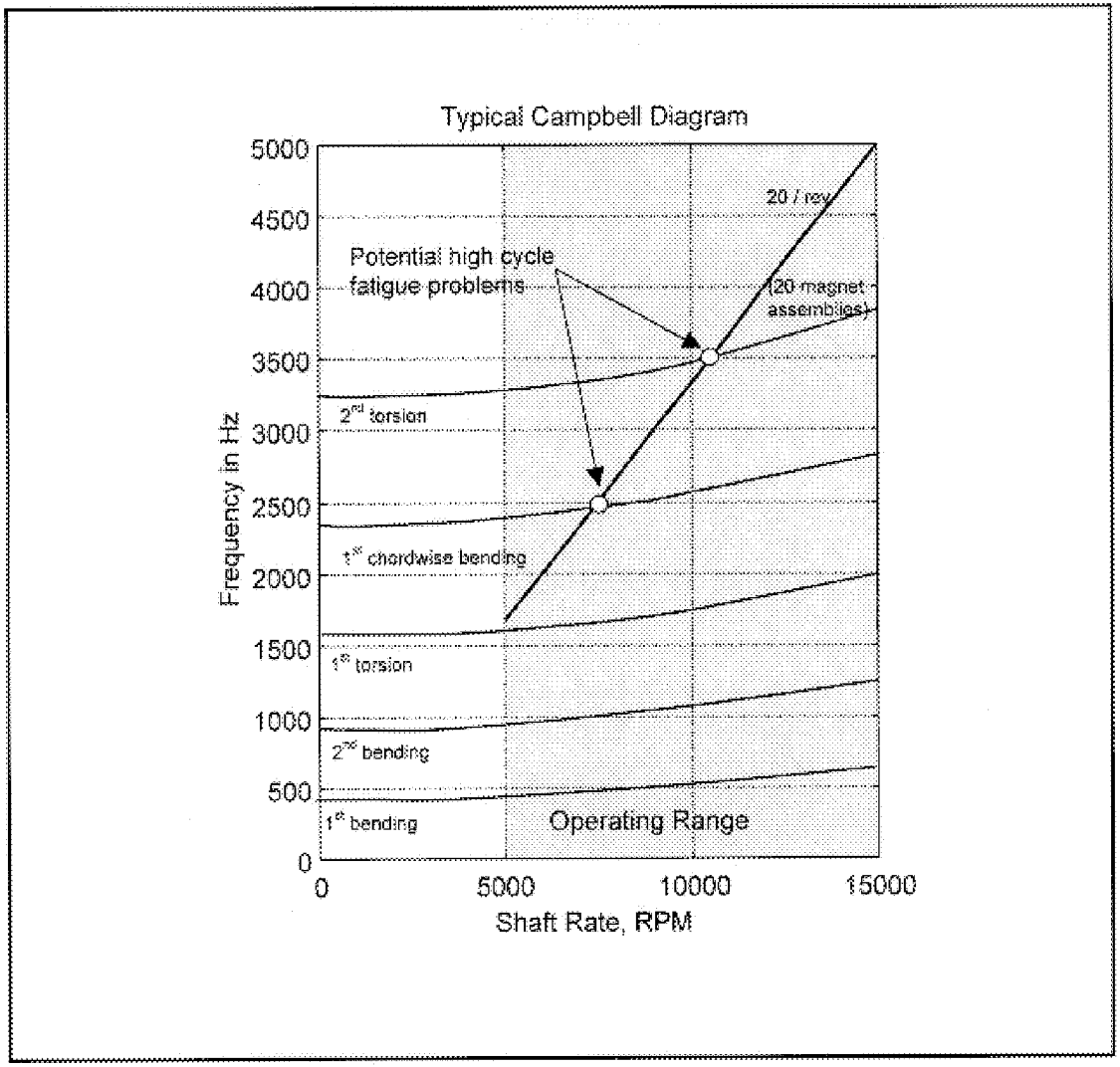
FIG. 5 shows a typical Campbell diagram. A stationary magnetic field excites blades at a multiple of shaft rate. A spinning magnetic field can excite blades with frequency independent of shaft rate.

The eddy current excitation system is intended to reproduce the vibrational disturbance created by unsteady wakes around stator vanes. That disturbance is synchronous with spool rotation, occurring N times per revolution, where N is the number of airflow impediments encountered every revolution. Due to inertial loading, blades resonate at frequencies that change with the rate of rotation. The Campbell diagram (FIG. 5) shows resonance as a function of shaft rate. On the same diagram, one can plot the excitation curves (NE, where E is the shaft rate). The intersection of a resonance and an excitation line corresponds to a potentially dangerous shaft rate where the synchronous excitation coincides with a blade resonance.

Magnet Location

Figure 6:
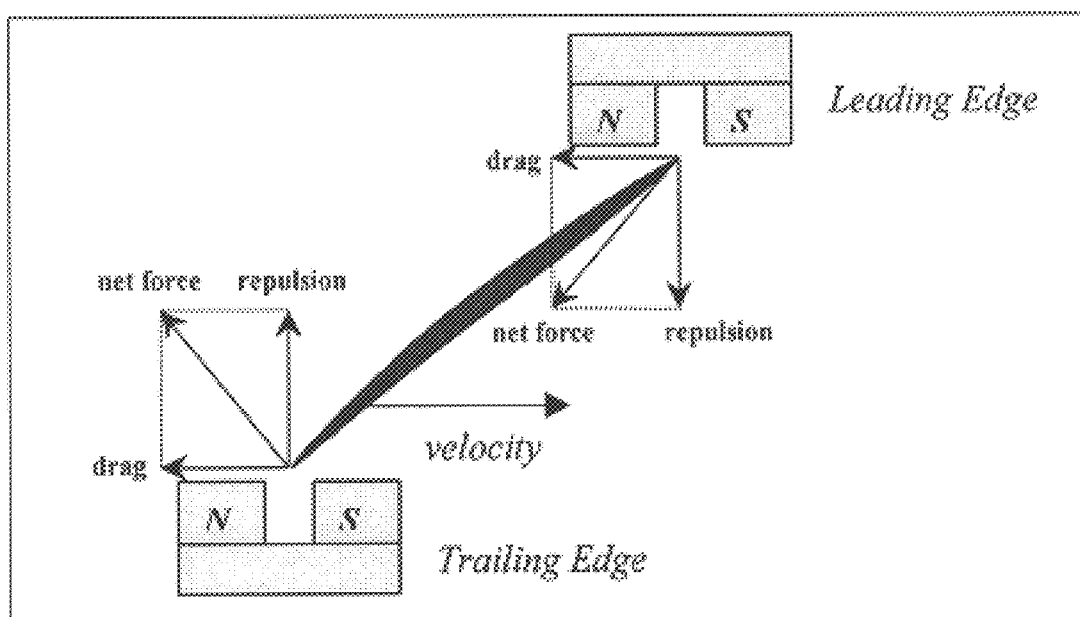
FIG. 6: Resultant of Eddy Current Forces. In order to excite blade vibration most effectively, eddy current forces should be perpendicular to the blade surface. Magnetic eddy currents create drag and repulsion forces. At the trailing edge, repulsion and drag sum to create a net force approximately perpendicular to the blade surface. At the leading edge, the forces sum to be almost parallel to the surface; so that the resulting force creates little vibration. At the blade tip, the drag force excites vibration, but the repulsive force has little effect.

In order to excite blade vibration most effectively, eddy current forces should be perpendicular to the blade surface. Magnetic eddy currents create drag and repulsion forces. At the trailing edge, repulsion and drag sum to create a net force approximately perpendicular to the blade surface. At the leading edge, the forces sum to be almost parallel to the surface; so that the resulting force creates little vibration. At the blade tip, the drag force excites vibration, but the repulsive force has little effect (see FIG. 6). The magnets are therefore best positioned at the trailing edge and at the tip of the blade.

The exact clocking of the various tip, trailing edge and mid-span magnet pairs can be further tuned to shape the pulse sequence and shape specific spatial/temporal force distributions to excite a given mode. We therefore make provision for clocking various magnet assemblies. This configuration is illustrated in FIG. 7.

While the invention has been described in connection with what is presently considered to be the most practical and preferred embodiments, it is to be understood that the invention is not limited to the disclosed embodiments, but on the contrary, is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated by reference in their entirety and relied upon.

What is claimed is:

1. A method for causing excitation of turbo-machinery blades that reproduces the vibrational effects of stator wakes and other inhomogeneous airflow, said method comprising positioning an array of magnets near turbo-machinery blades to generate eddy currents in the blades to produce forces upon the blades comparable to forces acting upon blades in an operating turbo-machine wherein said magnets are positioned at a trailing edge and at a tip of said blades.

2. The method of claim 1, wherein the magnets are positioned so as to obtain periodic vibration of the blades equivalent to that from stator wakes.

3. The method of claim 1, wherein the array of magnets are configured to appropriately phase an excitation force applied to various portions of the blades such that a selected target mode of vibration is strongly excited.

4. The method of claim 1, wherein magnets are repositioned relative to passing blades to control the excitation force.

5. The method of claim 1, wherein the array of magnets is designed with reference to a computational model of an unsteady magnetic interaction.

6. An apparatus for causing excitation of turbo-machinery blades that reproduces the vibrational effects of stator wakes and other inhomogeneous airflow, comprising means for generating eddy currents in the blades by an array of magnets to produce forces upon the blades comparable to forces acting upon blades in an operating turbo-machine wherein said magnets are positioned at a trailing edge and at a tip of said blades.

7. The apparatus of claim 6, wherein the magnets are positioned so as to obtain periodic vibration of the blades equivalent to that from stator wakes.

8. The apparatus of claim 6, wherein the array of magnets are configured to phase an excitation force applied to various portions of the blades such that a selected target mode of vibration is strongly excited.

9. The apparatus of claim 6, wherein magnets are repositioned relative to passing blades to control the excitation force.

10. The apparatus of claim 6, wherein the array of magnets is designed with reference to a computational model of an unsteady magnetic interaction.

* * * * *